(12) United States Patent
McKay

(10) Patent No.: US 8,763,278 B2
(45) Date of Patent: Jul. 1, 2014

(54) FOOTWEAR ASSEMBLY WITH INTEGRAL FOOTBED SUSPENSION SYSTEM

(75) Inventor: Norman McKay, North Vancouver (CA)

(73) Assignee: Plantiga Technologies, Inc., North Vancouver (CA)

( * ) Notice: Subject to any disclaimer, the term of this patent is extended or adjusted under 35 U.S.C. 154(b) by 638 days.

(21) Appl. No.: 12/990,490

(22) PCT Filed: May 1, 2009

(86) PCT No.: PCT/CA2009/000617
§ 371 (c)(1),
(2), (4) Date: Dec. 9, 2010

(87) PCT Pub. No.: WO2009/132465
PCT Pub. Date: Nov. 5, 2009

(65) Prior Publication Data
US 2011/0131836 A1    Jun. 9, 2011

Related U.S. Application Data

(60) Provisional application No. 61/049,751, filed on May 1, 2008.

(51) Int. Cl.
*A43B 7/14* (2006.01)
*A43B 3/24* (2006.01)

(52) U.S. Cl.
USPC ............... 36/93; 36/101; 36/114; 36/132

(58) Field of Classification Search
USPC .............. 36/93, 101, 132, 114, 97, 55, 1, 88
See application file for complete search history.

(56) References Cited

U.S. PATENT DOCUMENTS

| 3,154,866 | A | * | 11/1964 | Laufbahn | 36/101 |
| 4,322,893 | A | | 4/1982 | Halvorsen | |
| 4,858,341 | A | * | 8/1989 | Rosen | 36/97 |

(Continued)

FOREIGN PATENT DOCUMENTS

| DE | 102 40 530 A1 | 3/2004 |
| DE | 10 2006 059658 B3 | 3/2008 |
| JP | 05-293001 A | 11/1993 |

OTHER PUBLICATIONS

PCT International Search Report and PCT Written Opinion of the International Searching Authority dated Jul. 7, 2009 issued for the corresponding PCT Application No. PCT/CA2009/000617.

(Continued)

*Primary Examiner* — Ted Kavanaugh
(74) *Attorney, Agent, or Firm* — Fenwick & West LLP

(57) ABSTRACT

A footwear assembly with integral footbed suspension system is disclosed. A shoe comprises a sole, a blade extending away from the sole, an Energy Return System (ERS) connected to the blade, an upper, and a cradle coupled to the upper and coupled to the ERS via a plurality of ties, wherein the ERS is intermediate the cradle and the blade. The ERS is configured to resiliently deform under pressure from the foot while the foot is substantially suspended via the cradle relative to the sole. A plurality of sensors are configured to detect relative movement between components of the shoe and to transmit data to a chip positioned in the shoe. The data can be used for gait and performance analysis.

9 Claims, 12 Drawing Sheets

(56) References Cited

U.S. PATENT DOCUMENTS

| | | | |
|---|---|---|---|
| 5,060,402 A * | 10/1991 | Rosen | 36/97 |
| 5,282,325 A | 2/1994 | Beyl | |
| 5,357,696 A | 10/1994 | Gray et al. | |
| 5,533,280 A * | 7/1996 | Halliday | 36/101 |
| 6,195,921 B1 | 3/2001 | Truong | |
| 6,817,116 B2 * | 11/2004 | Chil et al. | 36/97 |
| 6,944,972 B2 | 9/2005 | Schmid | |
| 8,220,184 B2 * | 7/2012 | Albert | 36/101 |
| 2002/0174569 A1 * | 11/2002 | Tsai | 36/101 |
| 2005/0005472 A1 * | 1/2005 | Perenich | 36/27 |
| 2006/0000035 A1 * | 1/2006 | Kendall | 12/142 P |
| 2006/0021261 A1 * | 2/2006 | Face | 36/132 |
| 2007/0006489 A1 | 1/2007 | Case, Jr. et al. | |
| 2007/0180736 A1 * | 8/2007 | DiBenedetto et al. | 36/132 |
| 2008/0155861 A1 | 7/2008 | Lucas | |

OTHER PUBLICATIONS

PCT International Preliminary Report on Patentability dated Nov. 2, 2010 issued for the corresponding PCT Application No. PCT/CA2009/000617.

Applicant-provided Office Action issued for Japanese Patent Application No. 2011-506543, dated Aug. 20, 2013.

European Search Report issued for European Patent Appl. No. 09737607, dated Nov. 11, 2013.

* cited by examiner

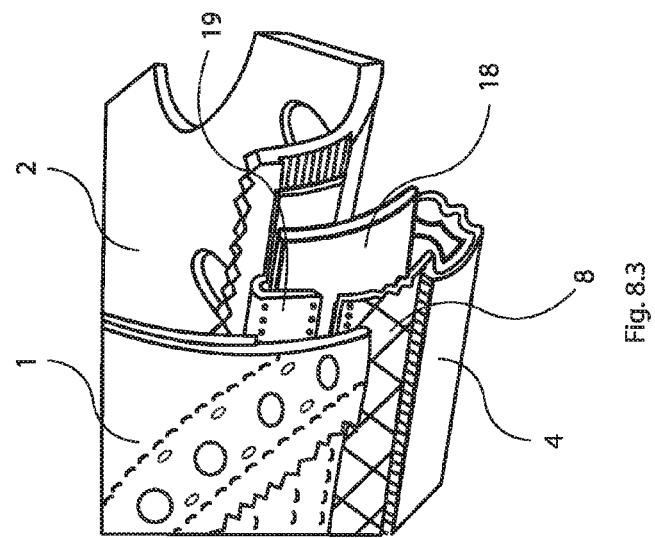
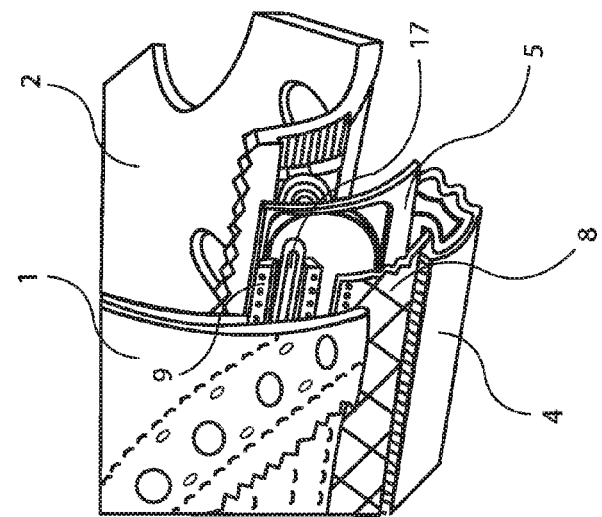
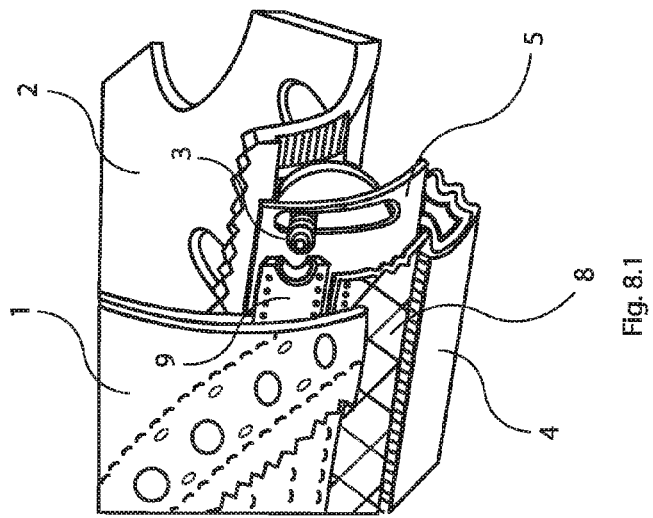
FIG. 8

FOOTWEAR ASSEMBLY WITH INTEGRAL FOOTBED SUSPENSION SYSTEM

CROSS-REFERENCE TO RELATED APPLICATIONS

This application is the U.S. national stage filing of PCT/CA2009/000617 filed on May 1, 2009, which claims priority to U.S. Patent Application No. 61/049,751 filed on May 1, 2008, entitled FOOTWEAR ASSEMBLY WITH INTEGRAL FOOTBED SUSPENSION SYSTEM, both of which are incorporated herein in its entirety by reference thereto.

TECHNICAL FIELD

The present disclosure is directed toward footwear, and more particularly to footwear with an integral footbed suspension system.

BACKGROUND

What is the problem (analog) with conventional shoes? Shoes do not actually work for you. They do not adapt to your moving about with loaded. There is nothing like a good human fit. In 100 years the "mold" has remained the same.

What is the problem (digital)? Analysis is typically only conducted with awkward equipment and only in the lab. It results in questionable (or subjective) data dumps. Further, static templates can be copied, lost, or stolen. It also provides very limited real-world sampling.

SUMMARY

What is the problem (analog) with conventional shoes? Shoes do not actually work for you. They do not adapt to your moving about with loaded. There is nothing like a good human fit. In 100 years the "mold" has remained the same.

What is the problem (digital)? Analysis is typically only conducted with awkward equipment and only in the lab. It results in questionable (or subjective) data dumps. Further, static templates can be copied, lost, or stolen. It also provides very limited real-world sampling.

BRIEF DESCRIPTION OF THE DRAWINGS

FIG. 8 is an illustration of a shoe assembly in accordance with the present disclosure.

DETAILED DESCRIPTION

Figure 1:
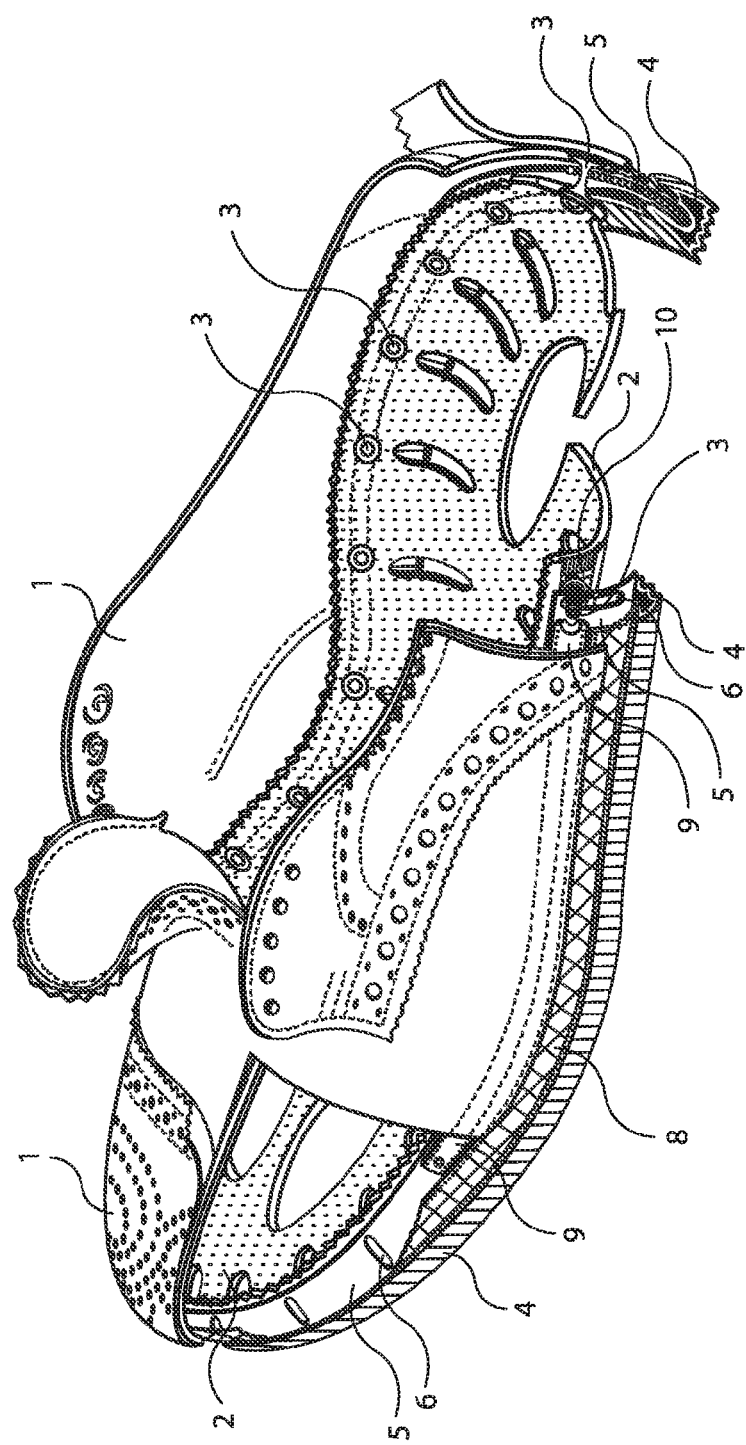
FIG. 1 is an illustration of a shoe assembly in accordance with the present disclosure.

A Basic Description of Our Footwear Mechanics
Overview of the Parts:

The new shoe is binary. It is separated into two regions of activity, with suspension of the human body as a physical differentiator, as illustrated in FIG. 1:

1) the body of the shoe: the upper 1 and the cradle 2 (the upper/Down under combination); and 2) the shoe's chassis: perimeter sole 4, blade 5, energy return system 12 (omitted from FIG. 1 for the sake of clarity) and sleeve 8.

Our footwear (footware, as we've called the new shoe) has broken the known way for manufacturing shoes, and introduced a new way for people to interact with their shoes. It's centered around a continuously changing form, as it will change according to how the user is acting as they go over the ground. The regular shoe is centered on using the last, with many people involved in the process, usually done in low pay areas around the world. Our shoe is not constructed this way.

Body

In one embodiment, the body of the shoe has the following construction:

Upper:

It 1 is made of leather or fabric or other materials, just like materials current uppers have.

The upper 1 is physically, dimensionally larger than the foot cradle 2, in both length and width. There needs to be enough of a size difference for energy return system 12+blade 5, as described below, to fit into this space (which we are calling Timing space).

It has a firm strip of material (a Rail 9), likely a nylon material (though many other polymers are possible choices), that runs around the leading edge of the upper, on the inside. This strip of material is attached—with glue, sewing or other means, and this strip may be composed of several parts.

It may be a part of a structural piece that's flush with the inner surface of the leather.

This strip is configured to anchor the narrow ties 3 that lie between it and the cradle 2.

Foot Cradle (the "Down Under"):

The Foot Cradle 2 is the foot bed, where the foot goes.

Figure 2:
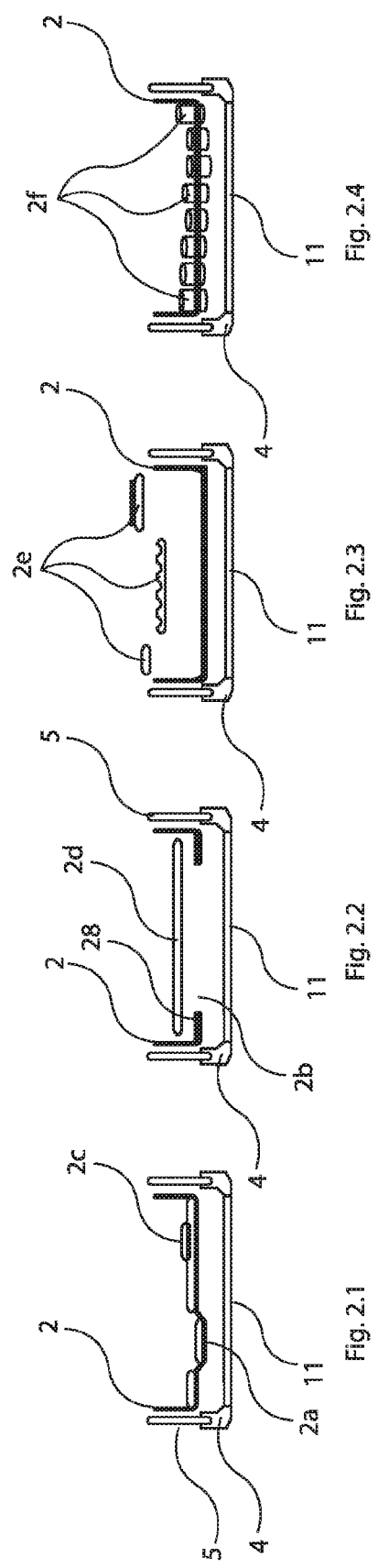
FIG. 2 is an illustration of a shoe assembly in accordance with the present disclosure.

It is like a hammock, sling, or carriage, in a basic physical description, but much more complex, in that it has the unique property of being responsive at varying locations along its perimeter as illustrated in the series of views of FIG. 2. These are called domain areas as they work with the tie 3 and other parts that lie in the same area at 'that point' within the shoe.

It can be designed to conform closely to the bottom of the foot.

It has a firm strip of material (rail 10), like that of the Upper, that runs around the perimeter, this time on the outside of this cradle 2.

This strip 10 parallels the strip 9 on the upper 1.

The cradle 2 could be built from various materials (nylon, woven mesh, gore tex, rubber . . . anything that can be thought of really, so long as it has the bed of it, with the bottom of it just to the other side of the bed, thus pointing to its material and all of it suspended).

This cradle 2 could have numerous embodiments and materials.

In cradle 2 construction, the forefoot, mid foot and rear foot can all have varying degrees of flexibility, stiffness or even hollowed out as depicted by 2a, 2b in views 2.1 and 2.2 or raised up parts 2c, 2d, 2e, 2f as shown in views 2.1, 2.2, 2.3 and 2.4.

It's possible to have different materials placed between the foot and cradle.

For instance, materials that add a rise 2c, 2d, 2e, 2f or that of a depression 2a, 2b can be added to the foot cradle 2 material.

In one embodiment, a ridge or horizontal shelf 28 will run around the foot cradle 2. This ridge 28 could have different materials with different strengths placed on it. This way you can have a variety of foot cradle materials/embodiments for specific foot conditions (see FIG. 2.2).

In another embodiment, of the above, the cradle 2 could be built with a type of 'long' hook system, for a place to snap-in the foot cradle.

Figure 3:
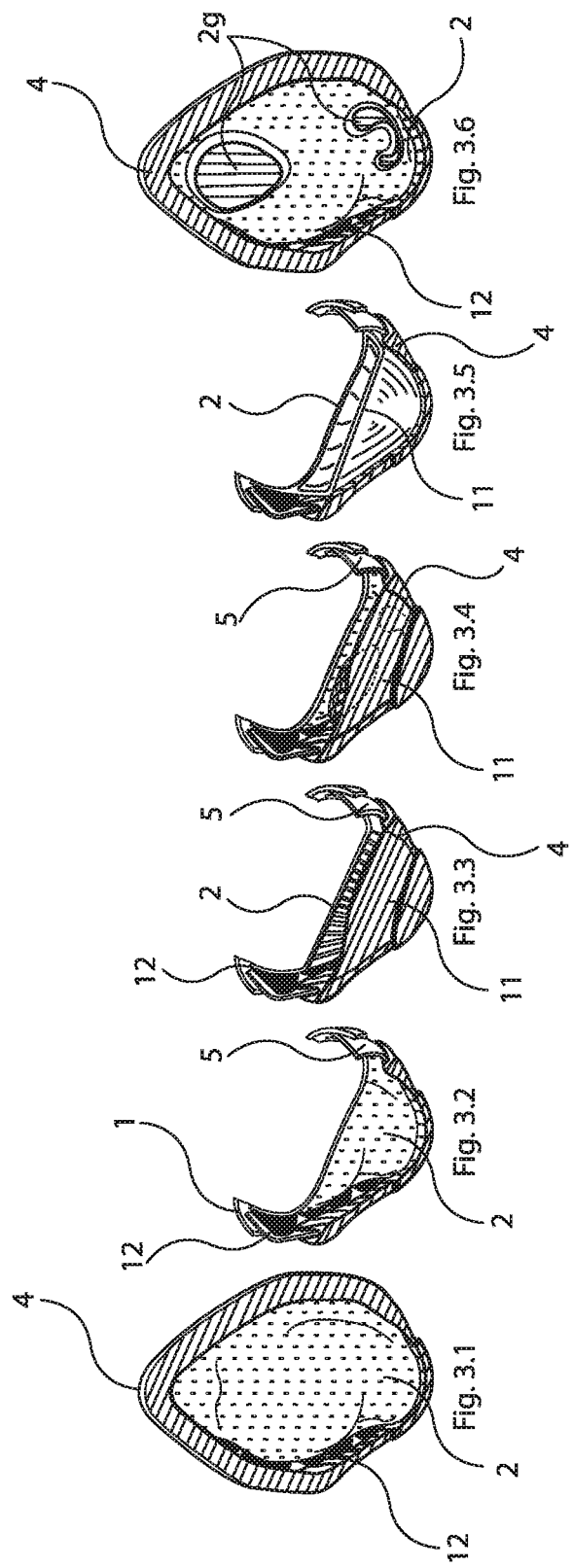
FIG. 3 is an illustration of a shoe assembly in accordance with the present disclosure.

The sides of the cradle 2 may be thinner than what is making up the foot bed. In fact this is amongst the most likely scenarios, as in these cases the rail 'part' 10 is now part of the sides of the cradle 2, as illustrated in FIG. 3. (In other words; the bed and bottom of a cradle is one thing, the sides and its rail another thing. One other embodiment.)

Each part is designable to various conditions and requirements.

As shown in FIG. 3:

3.1 This is an embodiment where no plate is being used. The entire shoe's contact is experienced through the perimeter sole 4, with its telemetry 'sent' to the sides of a foot; giving the foot a 'feel', just not the familiar one with hits to the bottom of the foot!

3.2 Emphasis on cradle 2 conforming to foot. Thick leather, stretchy material, anything that conforms to the foot.

3.3 In this embodiment both plate 11 and cradle 2 is emphasized. This cradle 2 shows how stiffness can be applied to the cradle 2, either partially or wholly.

3.4 In this embodiment the plate 11 can be built up. Depending on assessment the plate 11 could be built up in certain places only.

3.5 This embodiment shows how the cradle 2 and plate 11 could be built as one unit, with space between the two. This is as close as we come to a midsole. This embodiment would see the stiff plate 11 connected to, in someway, the foot cradle 2.

3.6 In this embodiment the foot cradle 2 is shown to have reinforcements placed in it. Or this could be a 'hollowed place' on the cradle. In back its built up on the inside.

Figure 4:
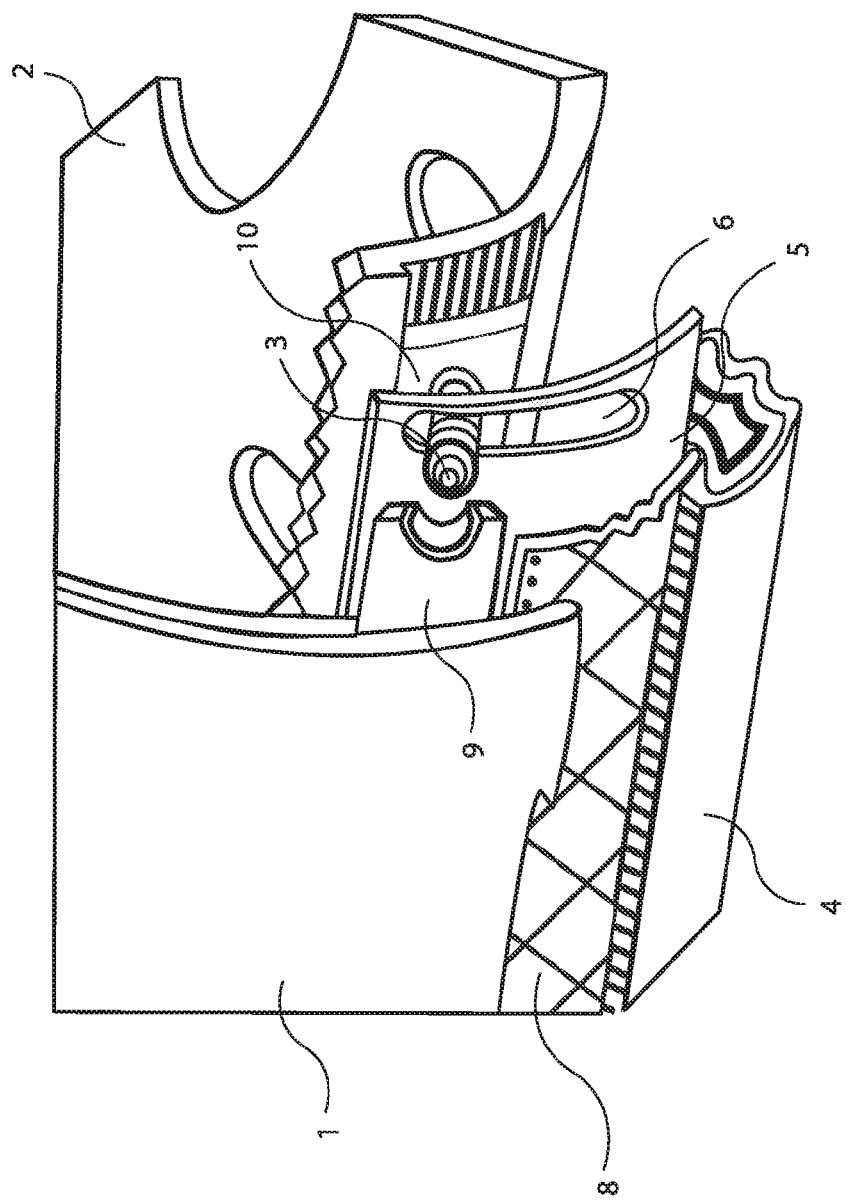
FIG. 4 is an illustration of a shoe assembly in accordance with the present disclosure.

Tie:

Ties 3 are narrow and short members that connect the upper 1 and foot cradle 2 together at various points around the shoe (see FIG. 4). Most likely they are fibrous and somewhat stiff.

They are most likely evenly distributed around the foot, but for the highly motivated they could be tied to where a person has a joint that needs particular attention. For the athlete these ties 3 would be adjustable; which would make all the domain parts adjustable too.

Ties 3 are connecting the larger upper 1 with the smaller foot cradle 2.

In other words; the ties 3 connect the cradle/carriage 2 to the upper 1.

It may be permanently attached to the upper 1 or foot cradle 2 through the stiff rails 9, 10 as illustrated in FIG. 4 (although rail 9 is omitted from FIG. 4 for the sake of clarity), or possibly made to hook, or slide, into a fixed area on the rail 9, 10.

Primarily the tie 3 will travel, under the load of a person, through the stiffening blade 5 and the energy return system 12 (not shown in FIG. 4).

The tie 3 moves vertically based on amplitude of force strike.

Chassis

Figure 5:
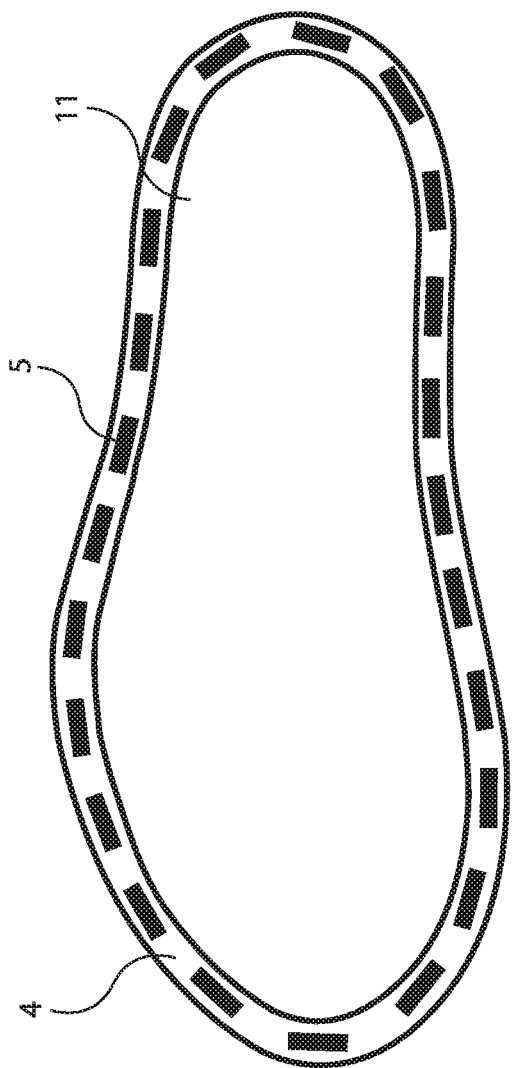
FIG. 5 is an illustration of a shoe assembly in accordance with the present disclosure.

Perimeter Sole (Illustrated in FIG. 5):

At its base the strike force is absorbed by this component 4.

At a basic level this is the part that reacts to the foot's strike force, as it now includes the reaction from the ground, the part of it directly beneath each tie's 3 (omitted from FIG. 5 for the sake of clarity) domain.

In one embodiment there may be a part (a foot Plate 11) that is housed within the perimeter sole 4, that will then add to the perimeter sole 4, making a full soled shoe In one embodiment, a full sole plate 11 can be screwed, clicked in, snapped on, etc., over the entire perimeter sole 4, on the outside of course.

The exterior portion of this sole plate 11 may be flexible (so it can bend over small extrusions (could be rocks etc.) of the grounds topography.

It could be segmented physically or have stiff portions connected with softer portions.

Segmentation could allow for partial rotation of the segments.

Segments could be inter-locked like a ball and joint, so they more readily grip various ground angles.

Note there is always space between the bottom of the foot cradle 2 and the top of the footplate 11.

Embedded in the rim of the perimeter sole 4, whether segmented or not, is a slightly wide, as a vertical measure, ribbon like blade 5 (see below also illustrated in FIG. 6).

In one embodiment the blade 5 can be sandwiched by the perimeter sole 4, meaning the perimeter sole 4 will have two edges. In some embodiments, we could have places along the blades length 5 where it has 'screwed in' axes, allowing a control of where it bends.

At the top of the perimeter sole 4, and on the inside, considering the blade 5, there is a groove or shelf that is set for the base of the energy return unit 12. In some manner this is set up to hold the base of the hard driver 12.

Figure 6:
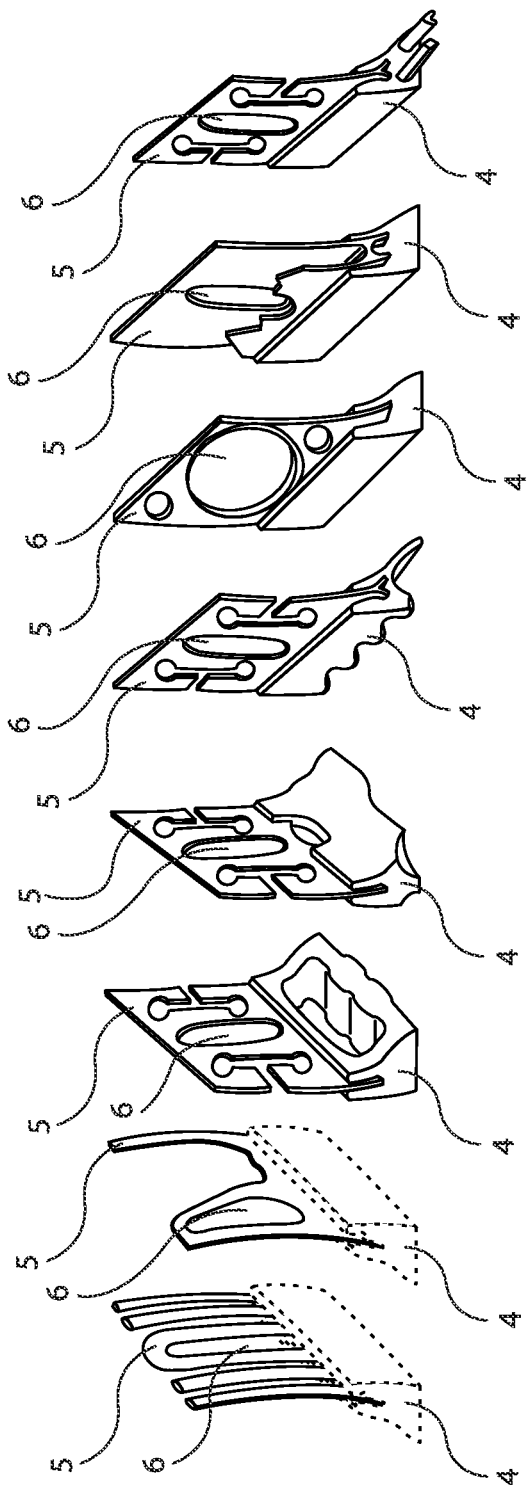
FIG. 6 is an illustration of a shoe assembly in accordance with the present disclosure.

Blade:

It is a vertical piece of plastic, also illustrated in FIG. 6, likely a nylon, that is embedded near the outer rim of the perimeter sole 4.

It may be removable from the perimeter sole 4, or not, and it may be segmented or not. It could have soft sections, for where the shoe bends.

For the most part it is required on both sides of the foot— the very front and back is not necessarily needed, as it bends in the perimeter sole 4 when both sides go one way—and then another—as the person plants their sole, at times, angled away from the vertical stance and movements This points to the duality of the blade 5, since it can angle itself, going from one direction to another, depending on how the foot is angling itself during a stride.

One major descriptive point: the upper portion, or zone, of this component fits between the upper 1 and cradle 2. The vertical portion of the blade 5, that is used for travel, fits between, usually, the bottom of the upper 1 and the top of the perimeter sole 4. This distance can be anywhere between a third of an inch and three quarters. The blade 5 will be even higher (two inches, or more) for military and army type boots, where more stability/control/strength is needed.

One of the main purposes for it is controlling for lateral instability.

Of central importance are the vertical cut-outs (slots) 6 in the blade 5 that act as a guide for the tie 3.

Each of these cut outs 6 guides the vertical travel of the tie 3. There is a cut out 6 for each tie 3.

Note that the cut-outs 6, also illustrated in FIG. 6, may be in a sliding portion, wafer thin, of the blade 5; or they may be in short sections, that once put together are making up a whole blade 5.

And note the cut-outs 6 may be in various shapes.

In the illustrated embodiment (see FIG. 6) there are three horizontal zones for the blade 5: one, the embedded part that fits in the perimeter sole 4; two, the mid zone where the body moves up and down against it; and three, the part that fits into the body parts of the shoe (in the Timing space).

The blade 5 can be a consistent height around the shoe, but can work/embrace different heights within the one shoe.

Energy Return System (the "Hard Drivers"):

As an overview of its purpose: each of the energy return systems 12, as in one unit, must have a specific impact strength that can receive the energy charge from the foot loading, and then return it as the pressure is lessened. This system transforms, in a sense interpreting, the forces that are being applied.

Figure 7:
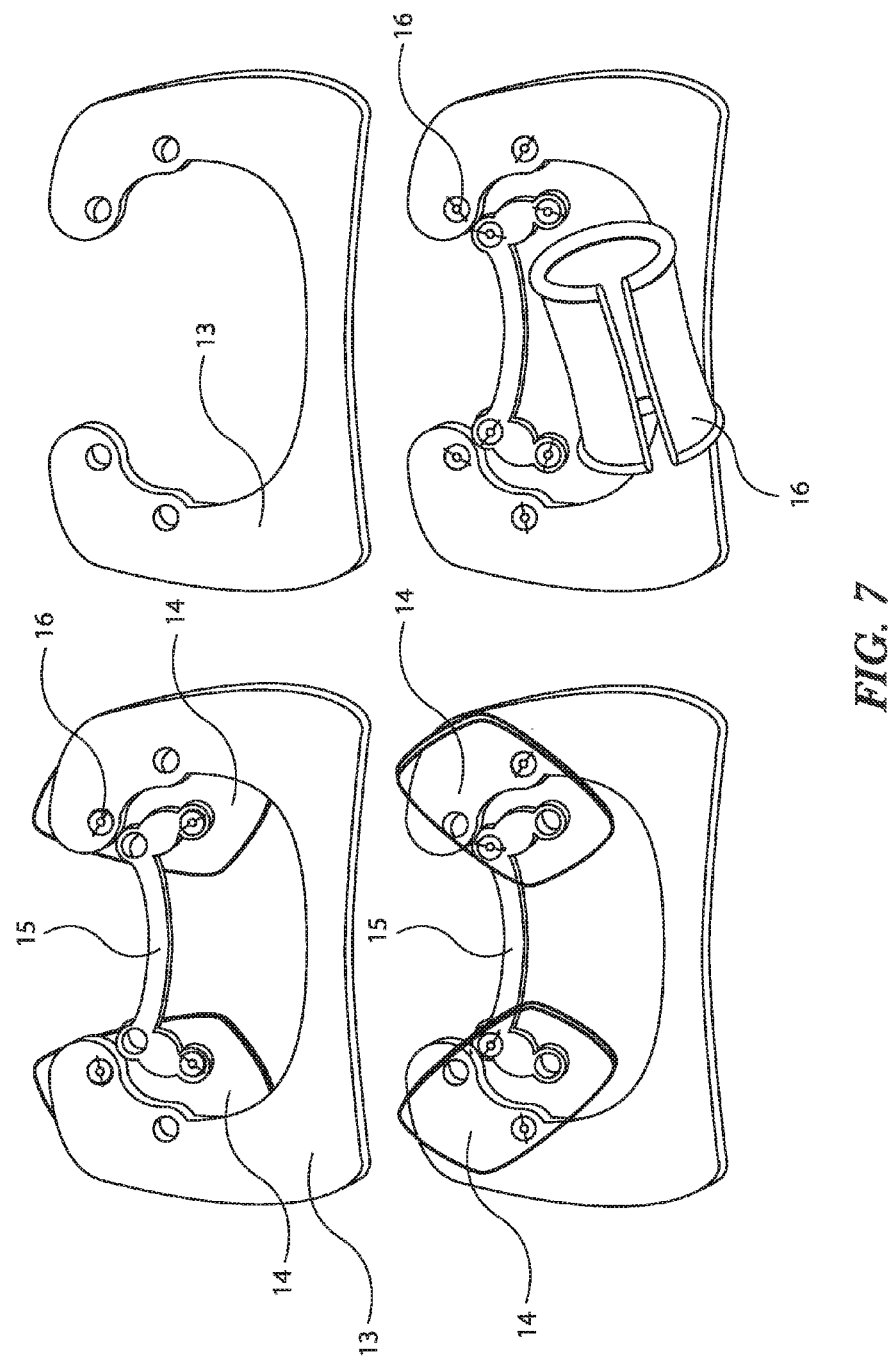
FIG. 7 is an illustration of a shoe assembly in accordance with the present disclosure.

Referring to FIG. 7, the ERS 12, or driver, has a wafer thin, vertical, and stiff frame 13; its open at the top with an interior space. This space is a zone, designed to allow the new shoe ties 3 traveling room within it. They can move vertically, though slight deviations are allowed. Ties 3 will go downwards first, against the resistance strength of the ERS 12, and then back up.

On both sides of this vertical frame 13 there are generally flat and extensible/tensor 14 polymer units (likely two to each side, one on either end of the opening—two on the inside and two on the outside of the frame 13).

Different strengths for the ERS units 12 are pointing to these tensor units 14. Thickness and lay-up of the polymers, with different amounts of carbon in the elastomer base, for instance, and even the size and thickness, as well as outer shape, will combine to produce ERS units 12 of varying strengths.

Between these tensor units 14 there is a semi pliable—somewhat stiff bridging unit 15 (wing) that lies within the interior space (flush on both sides). It's fibrous so it does not stretch. It should only bend.

The bridge unit 15 is what supports the tie 3, and thereby that portion of the human body's weight that is bearing down on just that particular area in the shoe (which, for us, are called domains: the tie 3 is the center and the immediately adjacent materials around it, regardless of what layer they are in, are a part of each domain).

The tensor units 14 are never pinned to each other, but only to the frame 13 with one lock-pin 16 and to the bridge unit 15 with another lock-pin 16.

All of the pins 16, the eight of them in the illustrated embodiment, are meant to allow rotations (small arcs) in tensor units 14, which allows and controls the down and up movements of the bridge 15.

There's a mathematical relationship between where the pins 16 are, both in the frame 13 and the bridge 15. A front tensor 14 will widen when the load is taken on, and the tensor 14 in back of it will lengthen. This process gives the pin 16 placements a kind of "X", or scissor action.

The arrangement allows one to maximize the tie 3 travel, while minimizing the distortion in tensor units 14.

It means the makeup of the polymers, the ones that make up the tensor units 14, are managed by making them stay within their plastic limit.

The tensor units 14 themselves can be designed in many ways—the size of the tensor units 14 can vary, as there is not much of a bounding limit (just the envelope of space we are calling Timing space). As well, the pins 16 too can be different diameters, and different thicknesses.

Figure 9:
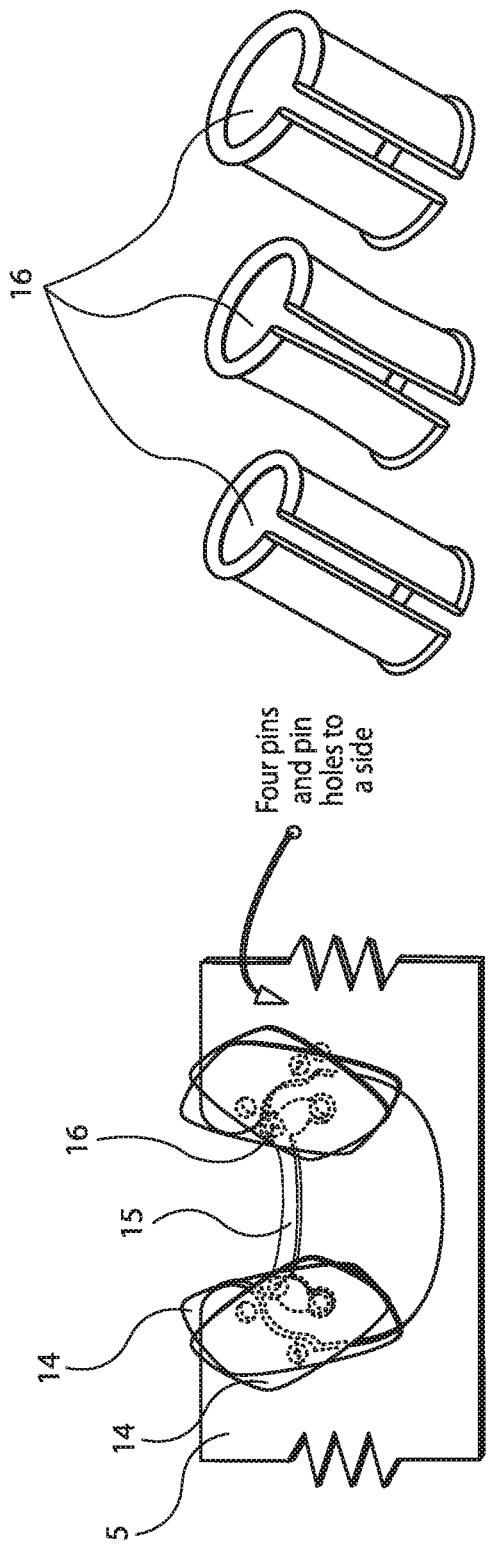
FIG. 9 is an illustration of a shoe assembly in accordance with the present disclosure.

The pins 16, illustrated in FIG. 9, right-hand view, can be lock pins 16 (our choice), and angled (like an hour glass) so as to lock in place, keeping locked the tensor unit 14, frame 13, bridge 15 combination.

Other embodiments for the energy return system 12 are varied (as shown below).

In one embodiment (see FIG. 8, far left 8.1) the tie 3 goes through an energy return system 12 (omitted from FIG. 8, but as described above).

In another embodiment (see FIG. 8, middle image 8.2) a short length of connector material 17 replaces the tie 3, the ERS 12 in this system longer and more like an amalgam of materials that may be likened to materials of today, that are already going into the makeup of a shoe.

In the last embodiment (See FIG. 8, right image 8.3) a belt system 18 replaces the unit type of energy return system 12. A belt system 18 might replace the need for the stabilizing blade 5, as it could incorporate stiffening units within it. An overhead clasp 19 would connect the foot cradle 2 and upper duo 1, 2 to the belt system 18.

In the embodiment below (see FIG. 9), the blade 5 and an energy return system 12 are built as one.

Figure 10:
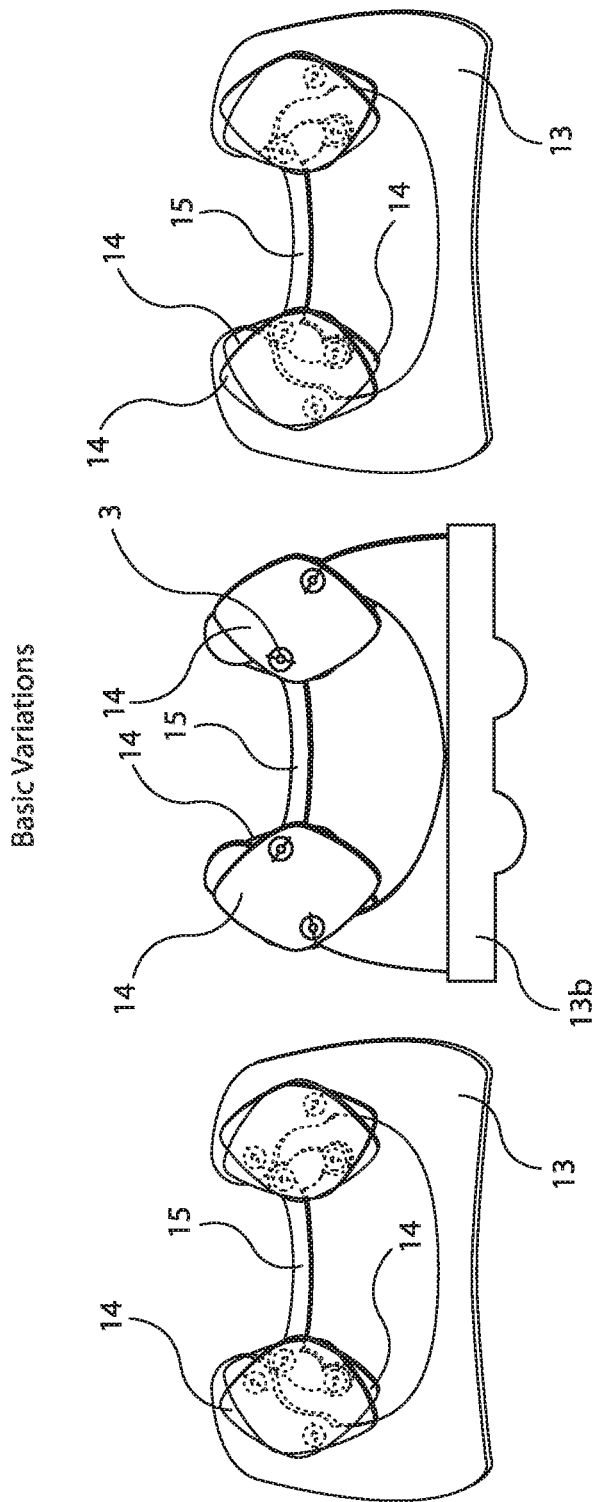
FIG. 10 is an illustration of a shoe assembly in accordance with the present disclosure.

In these embodiments (See FIG. 10, below), considered for the heaviest of duty footwear, the energy return systems 12 may be either reinforced with metal 13b, or completely built from it.

Figure 11:
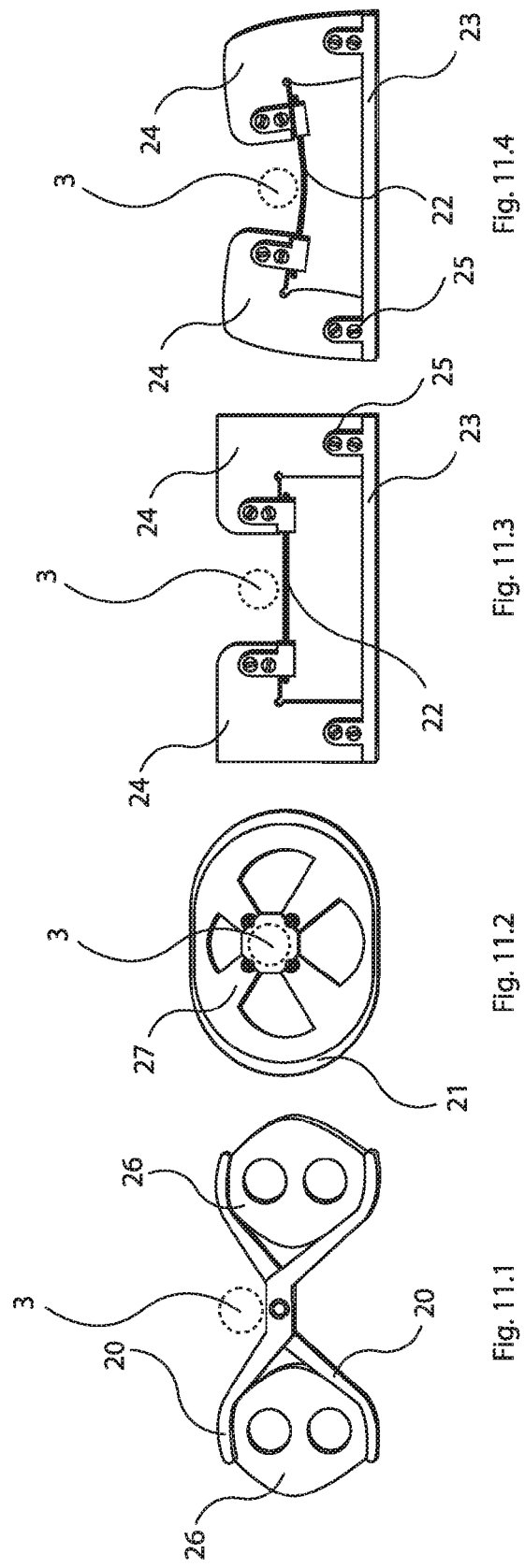
FIG. 11 is an illustration of a shoe assembly in accordance with the present disclosure.
Figure 12:
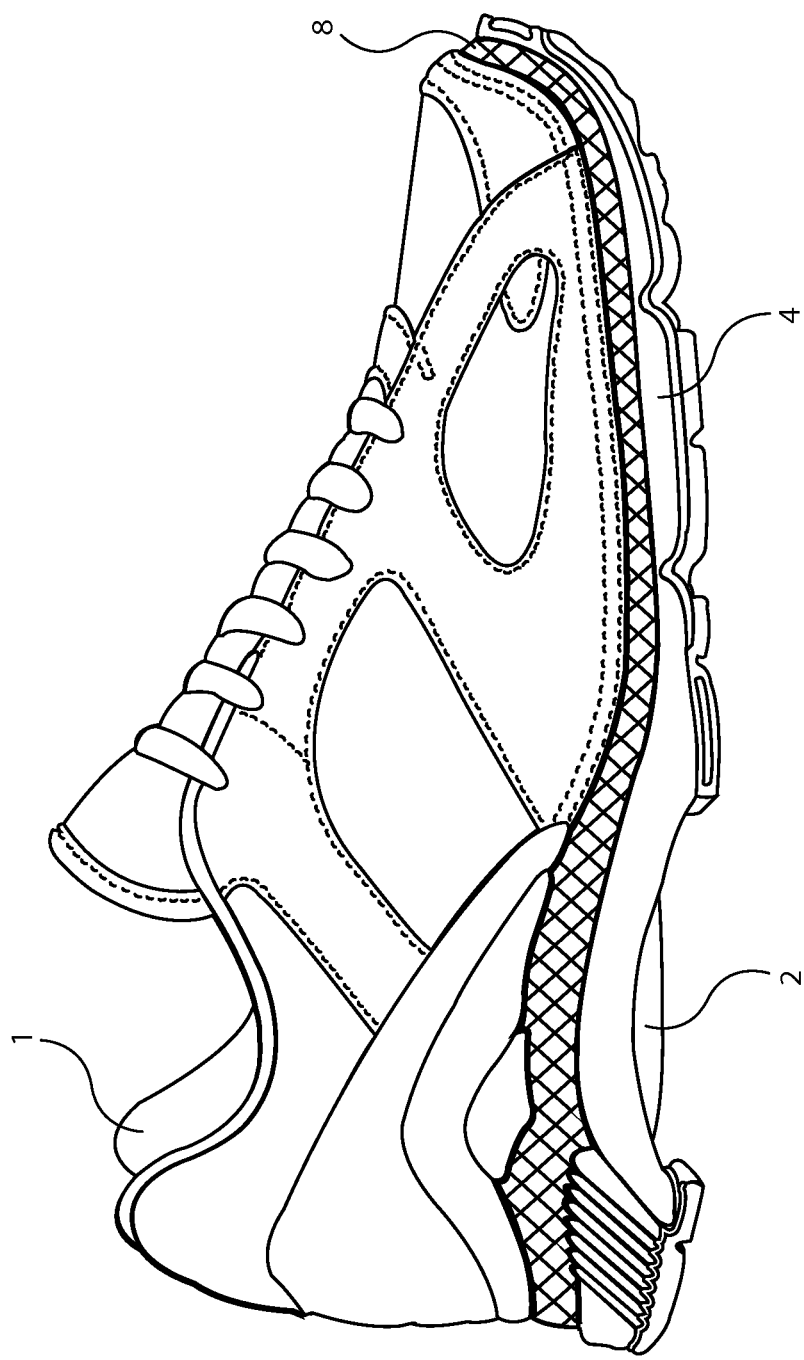
FIG. 12 is an illustration of a shoe assembly in accordance with the present disclosure.

In another embodiment (see FIG. 11, above left 11.1) there is a scissor-like version of the energy return system. Hard members 20 criss-cross to either side of the tie 3 (each of the four ERS's seen in FIG. 11.1 are showing an end view of one tie 3). Load actions will squeeze the polymer units 26 to either side of the tie 3, thus providing vertical travel. In the second embodiment (see FIG. 11, above middle 11.2) the tie 3 pulls at two of the arms 27 in the polymer mix, and simultaneously presses on two 27. A stiff frame 21 circles the whole unit.

In the third embodiment (see FIG. 11.3, 11.4, the two above right, showing a 'before' and 'after') the polymer body 24 bends (only with pressure applied), as the tie 3 sits over a semi-stiff bar 22 that also bends under the load pressure. Both polymer elements 24 here are held in place by a stiff bottom 23 (possibly metal), likely with pins 25.

Sleeve:

The sleeve 8 is there to cover for all of the inner workings (inner moving parts) and its pictured here in a wide red band, or ribbon. It's elastic in the main embodiment, probably waterproof, and it gets fixed within the leading edge of the upper 1 and against the side of the blade 5, between it and the inside edge of the perimeter sole 4, where it clasps the blade 5.

It circles the foot and covers the blade 5 (the central part of it that would otherwise bare).

It is ordinarily both flexible and elastic, but there are other embodiments where its under the upper 1 altogether. In this latter case the upper 1 is long on the sides, traveling down the outside of the perimeter sole 4 during loading and unloading in shoe action.

It allows breathability for the shoe, and ultimately the foot.

The material of the sleeve 8 could match that of the shoe, in both looks and functions; the specific environmental conditions expected are a part of the design brief.

It's up against the blade 5, but is not glued to it, or attached to it. The sleeve 8 can have a variety of designs.

In many commercial embodiments the upper's 1 leading edge is covering the mid zone of the blade 5, thus hiding the sleeve 8. When movement occurs the upper 1 will travel over the top of the perimeter sole 4 (as also mentioned just above).

Manufacturing:

Our footwear does not require it to be built on a last. Each of the components of the illustrated embodiments can be configured to be produced on a production line. When they are assembled, there will be little need to have a lot of people handling them. Much of it may even be done at point-of-sale, because, for many, the shoe is something that is fitted to their exacting requirements, both for functional and aesthetic reasons. Many will still want the appearance of the pre-assembled; so for these cases there can be a sort of 'dummy' shoe that would only need the drivers 12 inserted (with a special hand tool, designed just for this purpose), and some sort of trial period during the fitting stage.

So, yes, it can be pieced together, like on an assembly line.

The perimeter sole 4 can have a segmented configuration, either in short pieces, or in whole chunks covering a major portion of the shoe (the forefoot, say). Another segmentation might be 'soft' areas between harder ones, where the 'joint's' might act as couplings, similar to what lies between train cars. Or, we could have the perimeter sole 4 just a narrow version of what's already present in shoe soles, depending on the flexibility to interact with the blade 5 and body combined. If it was segmented it could be snapped together. The blade 5 could then be inserted, and the energy return devices 12, with ties 3, could be placed with the rail system 9, 10, already attached to their respective parts.

In another embodiment, our footwear is configured to shift what a show can do. The shoe and associated technology are configured to extend to analysis, identify and tracking.

The travel zone/region of our footwear is where the tie 3 that is connecting the upper 1 and cradle 2 together, moves through the energy return system 12. In an adult shoe there are (likely) 24 places of vertical travel.

When we monitor this vertical travel zone with a method that follows every incremental movement of each and every tie 3 as they go downward in the cut-out zone 6 and back up again, we will get a rich level of data. We might mark the travel using a feedback loop, transducer, etc. By doing so we have a data output of a large magnitude. All that is needed is some form of counter that marks the increments as they occur. Like a ruler, each point of vertical travel must be designed for capture, with calculated references. In the shoe each travel zone, within the cut-outs 6, can be noted to have, for instance, 300 dpi. This collected information, as the ties 3 moved along, at every travel zone is collected and sent to an ND converter/chip that would be best seen in one side of the shoe. The information can then be sent, wirelessly, to a central location with software, to analyze the generated data for various applications. Many applications will have this location within their smart phone. Others will have it within a station in a secured area for instance.

If we can think of every travel zone as having 10 places (theoretically like notches) of definable travel, and you multiple that by 24, you would get 24 to the power of 10 in possible mathematical outcomes in every given instance of one's foot cycle. That is one instance; when you take that amount of data and multiple that over a period of seconds or minutes, the richness of data output would be more than adequate for most all of our pictured applications.

With this richness of data, and once all of the noise and variables are logarithmically figured out, the data can be utilized for various applications.

With this data we will be able to locate, pinpoint and define patterns of walking and general movement. Once this occurs our footwear will then generate a behavioral biometric identity, based on the cadence of a stride. The users electronic ID in other words. But this is only the beginning. So many of these are possible, coming from the same collection of a person's travel, that they can have an ID that is different for one application than it is for another. Plus, this multiplicity of identifying numbers allows one to discard one, and then another one; anytime there is a chance for a compromise in the system they are sending it to.

I claim:

1. A footwear assembly, comprising:
    a sole;
    at least one blade attached to the sole and extending away from the sole and extending around at least a portion of a perimeter of the sole, the at least one blade having a plurality of substantially vertical slots;
    an upper;
    a cradle, a plurality of ties coupling the cradle with the upper, the cradle being generally shaped as a footbed and configured to receive a foot and to suspend the foot above the sole whereby the upper and the cradle are moveable as a unit relative to the sole;
    an energy return system coupled intermediate with the at least one blade and the cradle, the energy return system comprising at least one resilient, flexible member; wherein
    each of the plurality of ties passes through, and is arranged to move within, a corresponding one of the plurality of substantially vertical slots in the at least one blade to act upon the energy return system; and
    wherein the energy return system is configured to resiliently deform away from a rest position under pressure from the foot and to return to the rest position when the pressure is relieved so the upper and cradle can move with the user's foot independently from the sole.

2. The footwear assembly of claim 1, further comprising:
    an electronic chip positioned in the shoe and configured to record and transmit data; and
    a plurality of sensors positioned around the shoe and configured to detect relative movement between at least two of the ERS, the cradle, the ties, the blade, and the sole, the sensors being configured to transmit the data to the chip.

3. The footwear assembly of claim 2 wherein the chip is configured to transmit the data to a computing system for gait and performance analysis.

4. The footwear assembly of claim 2 wherein the energy return system comprises piezoelectric elements configured to deform under the pressure from the foot and convert the pressure into electricity to provide power to at least one of the sensors and the chip.

5. The footwear assembly of claim 1 wherein the energy return system comprises at least two resilient elements, and wherein the blade, the cradle, and the at least two resilient flexible elements are rotatably connected by the ties to form a linkage mechanism.

6. The footwear assembly of claim 1 wherein each of the at least one blade comprises:
    an embedded portion attaching the blade to the sole;
    a midzone extending above the sole, the midzone containing the plurality of substantially vertical slots; and
    an upper portion engages the upper.

7. The footwear assembly of claim 1 wherein the energy return system extends substantially around the perimeter of the sole.

8. The footwear assembly of claim 1 wherein the energy return system is configured to be interchanged with another energy return system with at least one of a different shape or resiliency.

9. A method of assembling a footwear assembly, the footwear assembly comprising:
- a sole;
- at least one blade having a plurality of substantially vertical slots;
- an upper;
- a cradle generally shaped as a footbed and configured to receive a foot of a user and, when assembled in the footwear assembly, to suspend the foot above the sole whereby the upper and the cradle are moveable as a unit relative the sole;
- an energy return system comprising at least one resilient, flexible member; and
- a plurality of ties;

wherein the method comprises:
attaching the at least one blade to the sole so that the at least one blade extends away from the sole and extends around at least a portion of a perimeter of the sole;
coupling the cradle with the upper using the plurality of ties, the at least one blade being coupled intermediate the cradle and the upper; and
coupling the energy return system intermediate with the at least one blade and the cradle so that each of the plurality of ties passes through, and is arranged to move within, a corresponding one of the plurality of substantially vertical slots in the at least one blade to be able to act upon the energy return system for the energy return system to deform away from a rest position under pressure from the foot of the user and to return to the rest position when the pressure is relieved so the upper and the cradle can move with the foot of the user independently from the sole.

* * * * *

UNITED STATES PATENT AND TRADEMARK OFFICE
CERTIFICATE OF CORRECTION

| | | |
|---|---|---|
| PATENT NO. | : 8,763,278 B2 | Page 1 of 1 |
| APPLICATION NO. | : 12/990490 | |
| DATED | : July 1, 2014 | |
| INVENTOR(S) | : Norman McKay | |

It is certified that error appears in the above-identified patent and that said Letters Patent is hereby corrected as shown below:

In the Claims

Column 8, line 43, after "at least two of the," delete "ERS" and insert -- energy return system --.

Column 8, line 55, after "at least two," delete "resilient elements" and insert -- of the resilient, flexible elements --.

Column 8, line 56, after "at least two of the resilient" insert -- , --.

Column 8, line 64, after "an upper portion," delete "engages" and insert -- engaging --.

Signed and Sealed this
Thirtieth Day of June, 2015

Michelle K. Lee
*Director of the United States Patent and Trademark Office*